(12) United States Patent
Aldridge et al.

(10) Patent No.: US 7,316,768 B2
(45) Date of Patent: Jan. 8, 2008

(54) GAS SENSOR AND METHOD OF MANUFACTURE

(75) Inventors: Roland Aldridge, Monrovia, CA (US); Steven Kirchnavy, Mission Viejo, CA (US); Hurbert Q. Stedman, Santa Ana, CA (US)

(73) Assignee: Advanced Micro Instruments, Inc., Huntington Beach, CA (US)

( * ) Notice: Subject to any disclaimer, the term of this patent is extended or adjusted under 35 U.S.C. 154(b) by 771 days.

(21) Appl. No.: 10/834,494

(22) Filed: Apr. 29, 2004

(65) Prior Publication Data

US 2005/0241938 A1    Nov. 3, 2005

(51) Int. Cl.
*G01N 27/40* (2006.01)

(52) U.S. Cl. ............... 204/431; 204/415; 204/432; 204/412

(58) Field of Classification Search ............ 204/431, 204/415, 432, 412
See application file for complete search history.

(56) References Cited

U.S. PATENT DOCUMENTS

| | | | | |
|---|---|---|---|---|
| 3,429,796 A | | 2/1969 | Lauer | |
| 3,767,552 A | * | 10/1973 | Lauer | 204/408 |
| 4,775,456 A | * | 10/1988 | Shah et al. | 204/412 |
| 5,338,429 A | * | 8/1994 | Jolson et al. | 204/415 |
| 5,667,653 A | * | 9/1997 | Schneider et al. | 204/431 |
| 5,702,576 A | * | 12/1997 | Kiesele et al. | 204/415 |
| 5,830,337 A | * | 11/1998 | Xu | 204/400 |
| 5,906,726 A | * | 5/1999 | Schneider et al. | 205/775 |
| 6,176,989 B1 | | 1/2001 | Shi | |
| 7,060,169 B2 | * | 6/2006 | Rohrl | 204/431 |

* cited by examiner

*Primary Examiner*—Nam Nguyen
*Assistant Examiner*—Surekha Vathyam
(74) *Attorney, Agent, or Firm*—John J. Connors; Connors & Assoc. Inc.

(57) ABSTRACT

A gas sensor comprises an electrically conductive housing including a shelf member and a chamber containing an electrolyte. A conductive cathode mounted on the shelf member has a plurality of holes therein and a conductive tail element. A gas permeable membrane overlying the cathode prevents electrolyte from escaping the chamber but allows gas to permeate the membrane. An anode within the chamber is in electrical contact with the electrolyte and the conductive housing. The tail element is adapted to be connected to the anode through an electrical circuit including the conductive housing.

37 Claims, 8 Drawing Sheets

GAS SENSOR AND METHOD OF MANUFACTURE

INCORPORATION BY REFERENCE

The inventors incorporate herein by reference any and all U.S. patents, U.S. patent applications, and other documents cited or referred to in this application or cited or referred to in the U.S. patents and U.S. patent applications incorporated herein by reference.

DEFINITIONS

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

BACKGROUND OF INVENTION

U.S. Pat. Nos. 3,429,796 and 6,176,989 disclose sensors that are replaceable units widely used with gas-analyzing instruments for measuring the amount of a specific gaseous constituent of a gas stream, for example oxygen in a methane gas stream. The operation of such sensors is based on an oxidation-reduction reaction occurring that causes an electrical current to flow between a cathode and anode within the sensor. The sensor is mounted to, or otherwise connected, in a fashion where a sample portion of gas from the gas stream flows into the sensor. The useful life of these sensors varies depending on the chemical composition of the gas being analyzed, the volume of sampled gas flowing into the sensor, the chemical composition of the cathode and anode of the sensor, and other factors. In the manufacture of these sensors defects frequently occur that create quality assurance problems.

SUMMARY OF INVENTION

This invention has one or more features as discussed subsequently herein. After reading the following section entitled "DETAILED DESCRIPTION OF SOME EMBODIMENTS OF THIS INVENTION," one will understand how the features of this invention provide its benefits. The benefits of this invention include, but are not limited to: a sensor having an extended useful life; a sensor having the same form, fit and function as conventional sensors, and therefore may be substituted for, or replace, conventional sensors; a sensor that is fast to condition; and a sensor that is highly reliable due to manufacturing processes that avoid or minimize defects.

Without limiting the scope of this invention as expressed by the claims that follow, some, but not necessarily all, of its features are:

One, the gas sensor of this invention includes a conductive housing having a chamber containing an electrolyte and a cathode and anode in contact with the electrolyte. The housing, being made of a metallic material, contributes to the benefits of this invention.

Two, the sensor has a first terminal including an electrical conducting member connected to the cathode that enables the sensor to make electrical contact with one contact of a gas-analyzing instrument. It also has a second terminal including an electrical conducting member that enables the sensor to make electrical contact with another contact of the gas-analyzing instrument. These first and second terminals provide means for connecting the cathode to the anode through an electrical circuit including the conductive housing upon use of the sensor with a gas-analyzing instrument. These terminals may be components of a circuit board attached to the housing.

Three, the housing may have different shapes, but in one embodiment it has a cylindrical configuration with a cylindrical sidewall that partially forms the chamber. The diameter of this cylindrical sidewall is from about 0.75 to about 2 inches and the thickness of the sidewall does not exceed about 3/16 inch. A portion of this cylindrical sidewall forming a part of the chamber has a minimum surface area of about 1 square inches, and may range from about 1 to about 5 square inches. The total volume of the chamber usually ranges between about 0.2 and about 2.5 cubic inches. In one embodiment, the housing has first and second opposed open ends that are closed and sealed when the chamber is filled with the electrolyte.

Four, a shelf member within the chamber may be used to support the cathode or anode or both. In one embodiment of this invention, the housing and shelf member are a unitary structure with the shelf member being integral with the sidewall, being disposed between the first and second opposed ends of the housing, and made from the same material as the housing. When the sidewall has a cylindrical configuration, the shelf member has a circular configuration and projects inward from the sidewall substantially at a right angle thereto. In one embodiment, the shelf member is annular, having an inner edge defining a central opening in the shelf member, a topside, and an underside. The topside may include a portion that slants inward towards the central opening.

Five, the cathode may be dome shaped and is open, usually having a plurality of holes therein. The cathode may include a conductive tail element. The cathode, and its tail element, may be made by conventional techniques such as, for example, stamping, machining, laser drilling, punching, photo-etching, and water jet drilling. The cathode may be mounted on the topside of the shelf member.

Six, a gas permeable membrane overlies the cathode and prevents electrolyte escaping the chamber but allows gas to permeate the membrane. At the interface between the membrane and the cathode a chemical reactions occurs resulting in a current flow. The holes are designed to enable ions to flow therethrough, and, for example, have a diameter of about 0.020 inch and are spaced apart about 0.020 inch. In one embodiment the tail element extends through an orifice in the sidewall and is insulated. The tail element may form in part the electrical conducting member connected to the cathode through the housing that enables the sensor to make electrical contact with one contact of a gas-analyzing instrument.

Seven, the cathode and membrane may be disposed between first and second compression elements, with the cathode and membrane each having an outer portion sandwiched between these compression elements. The cathode is isolated from the conductive housing and shelf member by an electrical insulating structure that may include the membrane. One of the compression elements may include a member with a rounded outer portion engaging the membrane during compression of the membrane. The other of these compression elements may be a component of the electrical insulating structure.

Eight, the compression element that is a component of the electrical insulating structure may include an outer annular spacer member, an inner annular member, and an "O" ring.

The outer annular spacer member is made of an insulating material and positioned on the shelf member. It may have first and second walls substantially at a right angle to each other, with the first wall abutting the sidewall of the housing and the second wall abutting the shelf member. The inner annular member is made of an insulating material and positioned on the shelf member and within the outer annular spacer member to be concentric therewith. The inner annular member is spaced from the second wall to provide an annular gap between the inner annular member and the second wall. The "O" ring is seated in this annular gap. Optionally, the second wall has a predetermined thickness, and the inner annular member has a thickness greater than this predetermined thickness of the second wall. This assists in forming or maintaining a dome shape of the cathode. The "O" ring seated in the annular gap is compressed to substantially fill this gap and provide a seal. The annular gap has a predetermined width, and the "O" ring, when in an uncompressed state, has a diameter that is less than the predetermined width of the annular gap.

Nine, the anode may be formed in place within the chamber (in situ). It is spaced from the cathode and may be, for example, mounted on and in electrical contact with the underside of the shelf member. The anode may have an aperture that is in communication with the opening in the shelf member. The opening and aperture may be concentric, and therefore, at least partially overlap. In one embodiment the anode is formed in situ in the chamber comprising compacted metallic particles. This anode is solid but porous.

Ten, a retainer structure may be employed that stretches the membrane. This retainer structure may comprise an inner member covering a central portion of the membrane and an outer member into which the inner member fits snugly. The membrane has a marginal edge portion that fits between the inner and outer members and is held firmly there between. The inner member is open to allow gas to permeate through the central portion of the membrane.

Eleven, the first and second ends of the housing may be capped with insulator members. These insulator members may be designed to fit over the edges of the ends and need not cover the entire open end. Their purpose is to electrically isolate the housing.

Twelve, the second end may include a flexible portion that expands and contracts as the temperature of the electrolyte changes to compensate for volumetric changes of the electrolyte.

Thirteen, in one embodiment, the sensor includes a pressure control structure adjacent to and overlying a side of the membrane that is not in intimate contact with the cathode. This pressure control structure forces the membrane into intimate contact with the cathode and is opened to allow gas to pass therethrough. The pressure control structure may comprise an outer, flexible metal disk-shaped spring member with openings therein that overlies a porous, disk-shaped cushion member.

The sensor of this invention may have a form, fit and function that is essentially identical to comparable conventional sensors, and therefore, it may be used to replace these conventional sensors as they wear out. The sensor's design and method of manufacture is, however, superior to conventional sensors because it has a longer useful life, takes less time to condition, and avoids or minimizes the creation of defects during manufacture.

These features are not listed in any rank order nor is this list intended to be exhaustive.

This invention also includes a method of manufacturing a gas sensor. This method comprises the steps of (a) forming a conductive opened ended housing with an chamber therein for containing an electrolyte, said housing having a shelf member extending into the chamber, (b) mounting an open cathode on one side of the shelf member and electrically insulting the cathode from the housing and shelf member, (c) placing over the cathode a gas permeable membrane that prevents electrolyte escaping the chamber but allows gas to permeate the membrane, and (d) inverting the housing to expose another side of the shelf member and forming in situ on said another side an anode, and (e) filling the chamber with electrolyte and sealing said chamber.

DESCRIPTION OF DRAWING

Some embodiments of this invention, illustrating all its features, will now be discussed in detail. These embodiments depict the novel and non-obvious gas sensor and method of manufacture of this invention as shown in the accompanying drawing, which is for illustrative purposes only. This drawing includes the following figures (FIGS. ), with like numerals indicating like parts:

FIG. 4 is a cross-sectional view of the assembled gas entry section inverted and with a plug in placed to assist in forming in place (in situ) an anode of the gas sensor;

FIG. 5 is a cross-sectional view of the assembled gas entry section of the gas sensor with the anode formed and electrolyte introduced into a chamber in the gas sensor;

FIG. 6 is a cross-sectional view of some of the components of the closure section of the gas sensor shown in FIG. 1 being assembled.

DETAILED DESCRIPTION OF SOME EMBODIMENTS OF THIS INVENTION

In General

Figure 1:
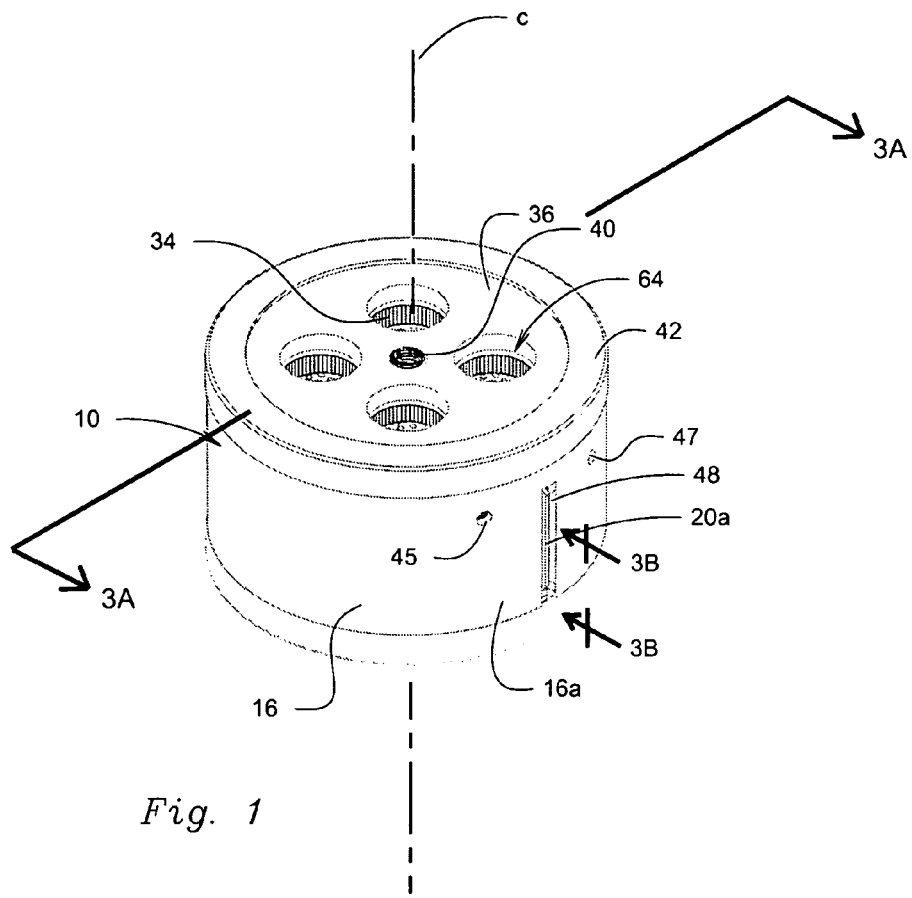
FIG. 1 is a perspective view of one embodiment of the gas sensor of this invention.

One embodiment of the gas sensor 10 of this invention includes a gas entry section 12 (FIG. 2A) and a closure section 14 (FIG. 2B) connected to the gas entry section. The gas entry section 12 may include the following components: (a) a cylindrical conductive housing 16 forming in part a chamber 18 (FIG. 3A), (b) a shelf member 16d integral with the housing, (c) a perforated, desirably substantially domed shaped, metal cathode 20 having a connector tail element 20a, (d) a seal seat 26 made of an insulator material, (e) an "O" ring 28, (f) a thin wall, gas permeable, non-conductive membrane 30, (g) a holding ring element 32, (h) a retainer plate 34, (i) a cover plate 36, (j) a C-clip 38, (k) a set screw 40, and (l) an annular, insulator end cap 42.

The cathode 20 is mounted on the shelf member 16d and is isolated from the conductive housing 16, including the shelf member, by an electrical insulating structure including the seal seat 26 and the membrane 30. The seal seat 26 and the retainer plate 34 provides a pair of compression elements, and the cathode 20 and membrane 30 each have an outer portion sandwiched between these compression elements.

Figure 3A:
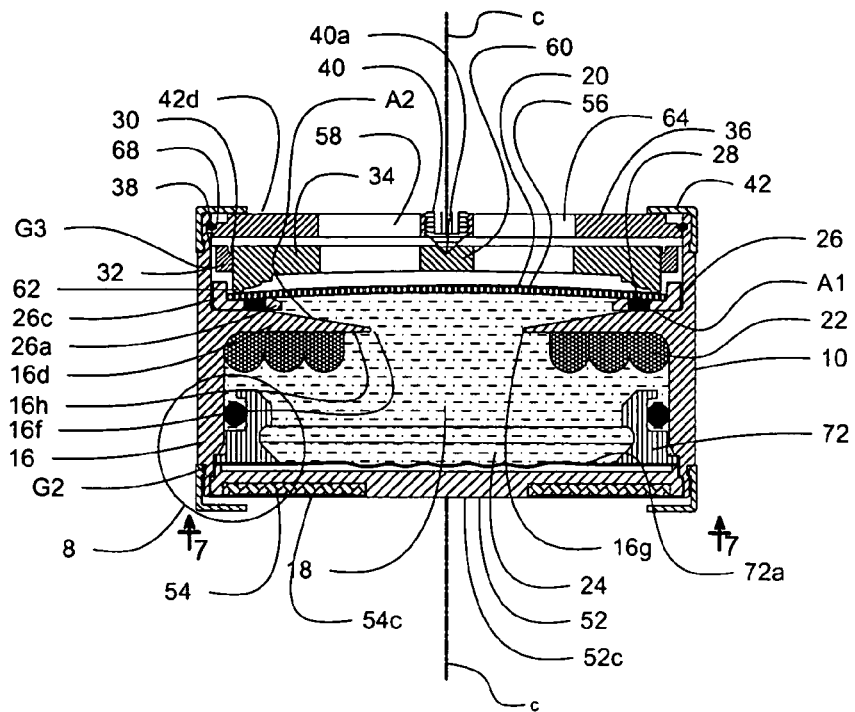
FIG. 3A is a cross-sectional view taken along line 3A-3A of FIG. 1.
Figure 3B:
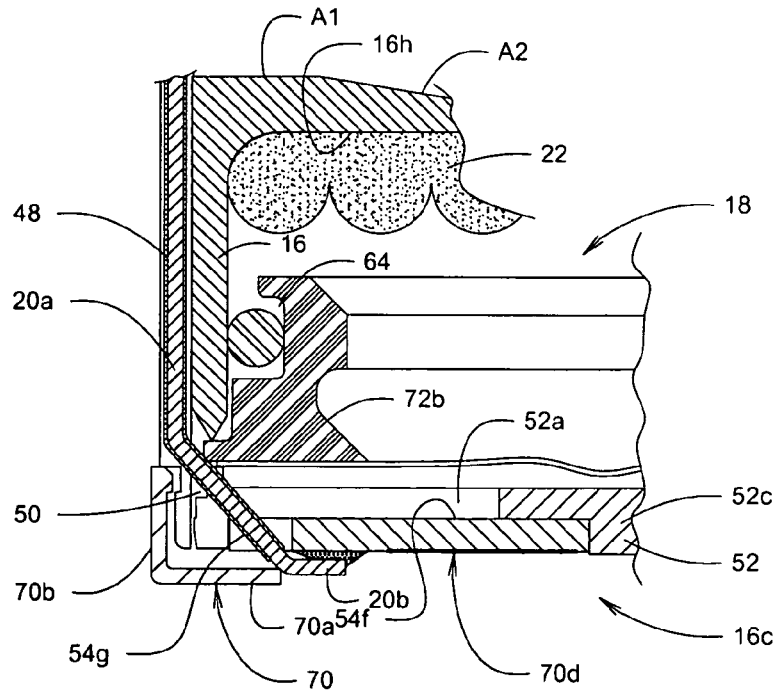
FIG. 3B is an enlarged, fragmentary cross-sectional view taken along line 3B-3B of FIG. 1.
Figure 4:
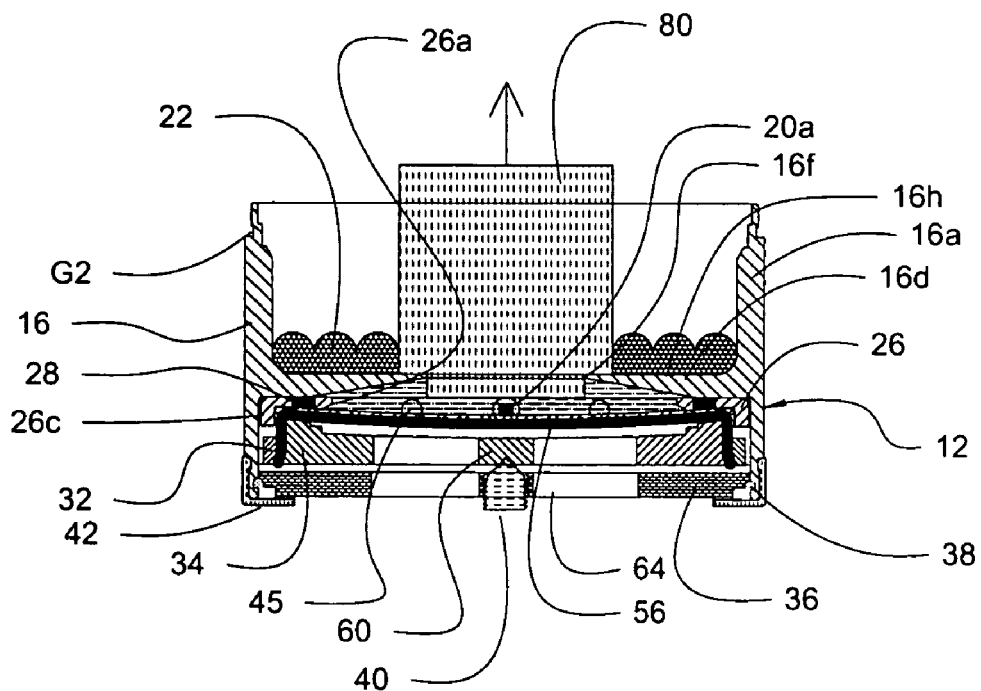
FIGS. 4 through 6 depict the closure section of the gas sensor of this invention being assembled where
Figure 5:
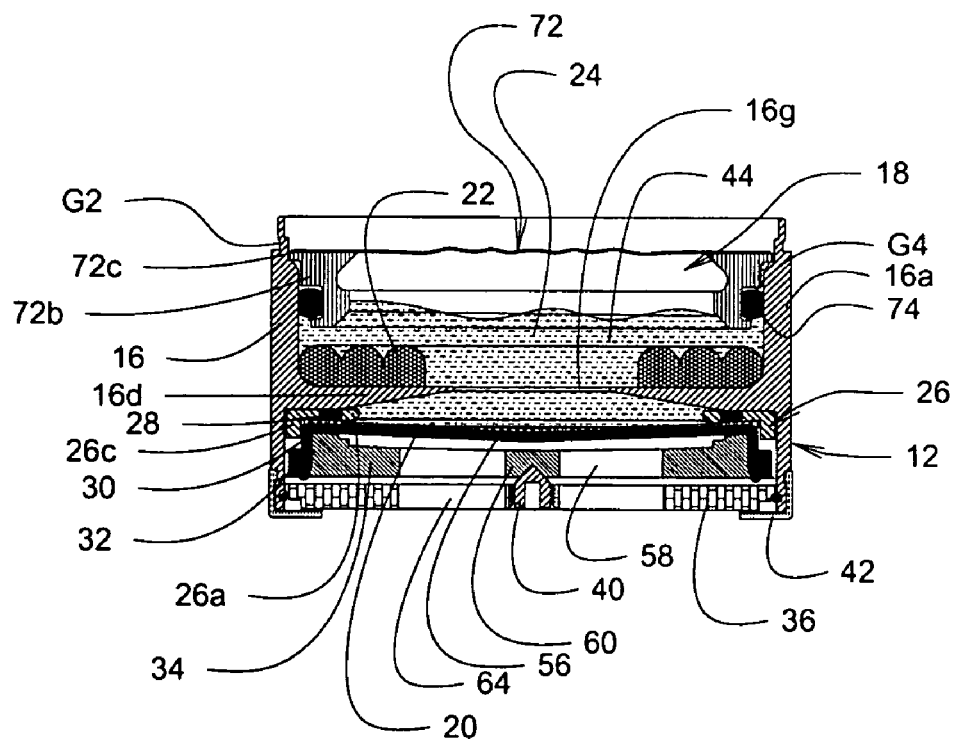
Figure 6:
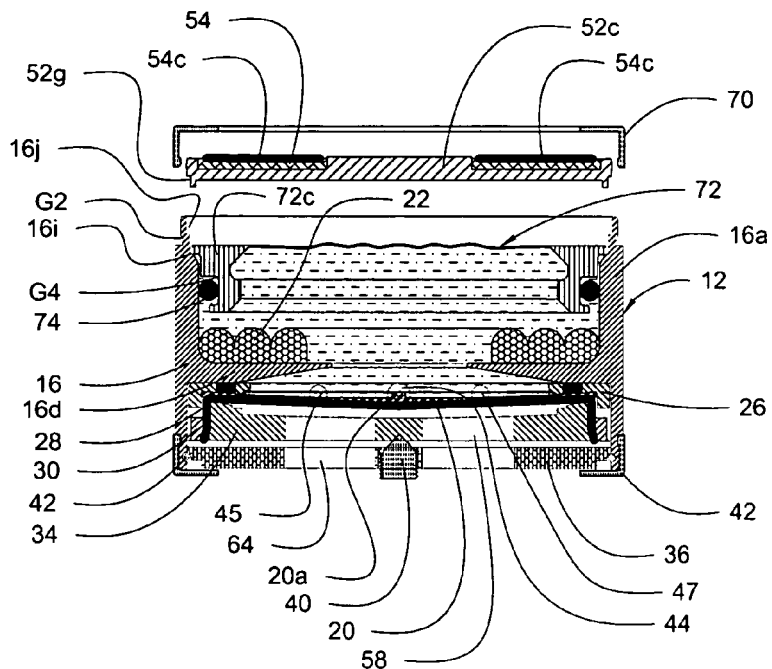

After assembling the components of the gas entry section 12, the gas entry section is inverted as shown in FIG. 4 and, as shown in FIG. 5, an anode 22 is formed in situ in the chamber 18. The anode 22 is spaced from the cathode 20 and is in electrical contact with the electrolyte 24 and the conductive housing 16 through the shelf member 16d. As shown in FIG. 6, with electrolyte 24 in the chamber 18, the closure section 14, which includes a gold plated conductive contact plate 52 and a disk shaped circuit board 54, is connected to the housing 16. As shown in FIG. 1, a portion of the tail element 20a extends through one part of a sidewall 16a of the conductive housing 16 that is above the chamber 18 and has a terminal end 20b (FIG. 3B) extending back through another part of the sidewall 16a below the chamber. This terminal end 20b is connected, for example by soldering, to an annular, gold plated conductive lead 54a along the periphery of the circuit board 54. This annular conductive lead 54a forms one terminal of the sensor 10 and a central circular shaped, outwardly projecting flange 52c (FIGS. 3A and 7) of the contact plate 52 forms another terminal of the sensor 10.

When the sensor 10 is used, its terminals, the annular conductive lead 54a and the outwardly projecting flange 52c, are each electrically connected to one of a pair of contacts of a gas-analyzing instrument such as, for example, disclosed by the inventors in U.S. patent application Ser. No. 10/106,635, filed Mar. 26, 2002, now U.S. Pat. No. 6,675, 629 B2. The sensor 10, upon its connection to a gas-analyzing instrument, collects in the chamber 18 a sample portion of the gas being analyzed. An oxidation-reduction reaction occurs within the chamber 18 that produces an electrical current that flows between cathode 20 and the anode 22 through a path including the housing 16 and the gas-analyzing instrument. The magnitude of this current is in proportion to the amount of the gas constituent being measured in the gas sample portion permeating the membrane 30. This reaction occurs at the interface between the membrane 30 and the cathode 20; the greater the amount of gas constituent in the sample portion of the gas, the greater the magnitude of the current.

The use of the conductive, metallic housing 16 enables the sensor 10 to hold about twice as much electrolyte as a comparable sensor not using a conductive housing but having the same form, fit and function. This primarily is due to the use of a metal to make the housing 16. A metallic housing 16 is much stronger normally than a non-metallic housing and therefore may have a relatively thin wall, for example, the sidewall 16a may only have a maximum thickness $t_3$ of about 3/16 inch, ranging, for example, from about 0.03 to about 3/16 inch. A comparable sensor not using a metallic housing but having the same form, fit and function typically has a minimum housing wall thickness greater than about 3/16 inch. Consequently, the sensor of this invention has a useful life about two times that of such a comparable sensor not using a metallic housing but having the same form, fit and function. The use of a metallic housing provides strength and gives one the ability to reduce the time to condition the sensor and extend its useful life as discussed subsequently.

The sensor 10 of this invention may be designed to analyze the amount of oxygen in a gas stream. In such instance, the housing 16 and the cathode 20 may be made of, or plated with, a precious metal, for example, silver, gold, rhodium and the like, and the anode 22 may be made of, or plated with, lead, zinc, cadmium. The housing 16 and the cathode 20 may be made of different metals, for example, the housing may be plated with rhodium and the cathode may be silver-plated. The electrolyte 24 may be an aqueous solution of, for example, sodium or potassium carbonate, phosphoric acid, or organic acids such as, for example, citric or ascorbic acid. When measuring oxygen in a methane gas stream, the anode 22 may be lead and the electrolyte 24 may be potassium hydroxide.

Normally the sensor 10 is stored until use in a sealed plastic bag, or the like, to prevent oxygen from entering the sensor. When the sensor 10 is exposed to the atmosphere upon connecting it to a gas-analyzing instrument, superfluous oxygen enters the chamber 18. Consequently, the gas-analyzing instrument, prior to use, is conditioned by passing an oxygen-free gas through the instrument and into the sensor 10 for a sufficient period until this superfluous oxygen has been consumed so that the instrument will indicate that there is essentially no oxygen present. Because of the conductive housing 16, an internal current between the cathode 20 and anode 22 is created that consumes superfluous oxygen. Therefore, the time it takes to condition the gas-analyzing instrument is reduced, mainly due the enlarged surface area provided by the conductive housing. Because the thin walled metallic housing 16 enables the chamber 18 to have a volume substantially greater than that of a comparable sensor not using a conductive housing, the useful life of the sensor 10 is extended over that of a comparable sensor not using a conductive housing but having the same form, fit and function. Evaporation of the electrolyte is one factor controlling the useful life of these types of sensors. Because the chamber 18 of sensor of this invention has a greater volume than like-sized sensors having the same form, fit and function, the sensor of this invention has a longer useful life than such like-sized sensors having the same form, fit and function.

The Gas Entry Section's Components

Figure 8:
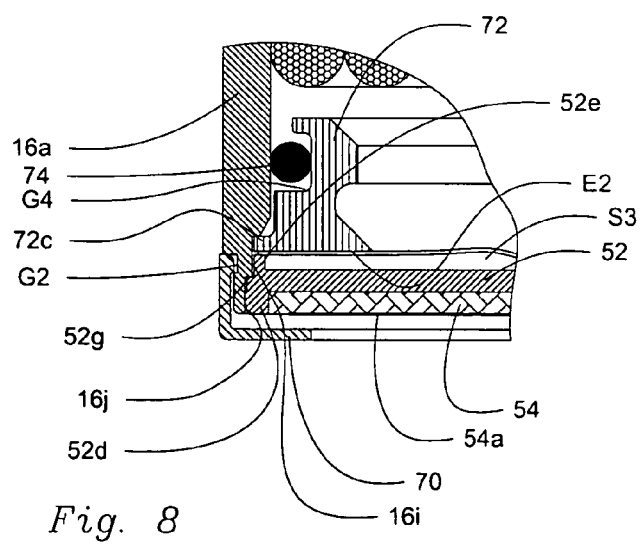
FIG. 8 is an enlarged, fragmentary cross-sectional view encircled within line 8 of FIG. 3A.

As best shown in FIGS. 1 and 3A and 3B, the cylindrical housing 16 is made of a conductive material such as, for example, silver plated brass. The housing 16 includes the sidewall 16a with opposed open ends 16b and 16c. The housing 16 and the shelf member 16d are a unitary, integral structure and the shelf member projects inward from the sidewall 16a substantially at a right angle to the sidewall. As discussed subsequently in greater detail, the open ends 16b and 16c of the housing 16 are closed and sealed so the chamber 18 retains therein the electrolyte 24. The shelf member 16d has an annular configuration and is intermediate the opposed open ends 16b and 16c. There is on the outside surface of the housing 16 annular grooves G1 and G2 respectively next to each open end 16b and 16c, and on the inside surface of the housing is an annular groove G3 next to the open end 16b. Extending through the sidewall 16a immediately above the shelf member 16d are spaced apart orifices 44, 45, 46, and 47. On the exterior of the sidewall 16a is an elongated recess 48 that is parallel to the central axis C of the sensor 10. The orifice 44 is in communication with the recess 48 near one end of the recess, and an orifice 50 (FIG. 3B) in the sidewall 16a beneath the shelf member 16d is in communication with the recess 48. As shown in FIG. 8, on the interior of the sidewall 16a near the end 16c is an inner annular ledge 16i and an outer annular ledge 16j.

The shelf member 16d is integrally formed with the sidewall 16a, for example, by machining or casting. It has a topside surface 16e including an outer, substantially flat annular platform area A1 and an annular inner, tapered area A2 slanting inwardly and downwardly, terminating in a circular edge 16f defining a central opening 16g in the shelf member 16d. It also has a substantially flat, annular underside surface 16h to which is bonded the anode 22 formed in situ in an annular configuration as discussed subsequently in greater detail in connection with the assembly of the closure section 14.

Figure 3C:
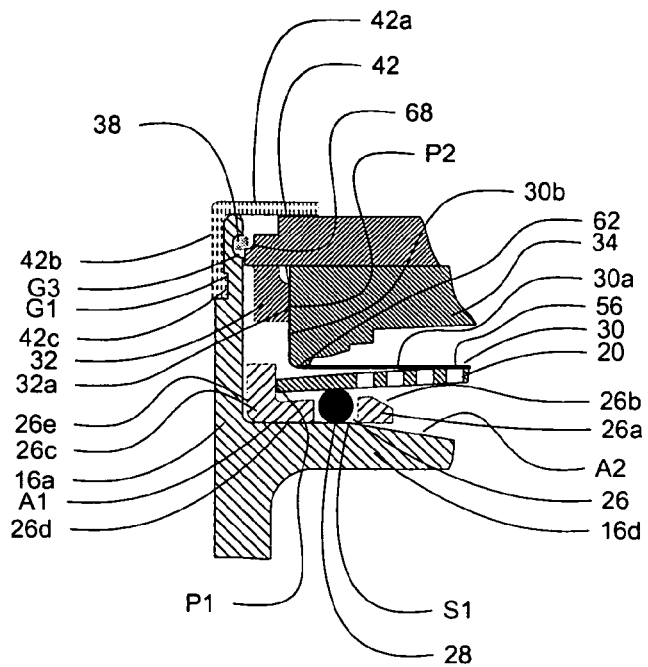
FIG. 3C is an enlarged, fragmentary cross-sectional view showing an "O" ring positioned in a seal seat of the gas entry section prior to being compressed.
Figure 3D:
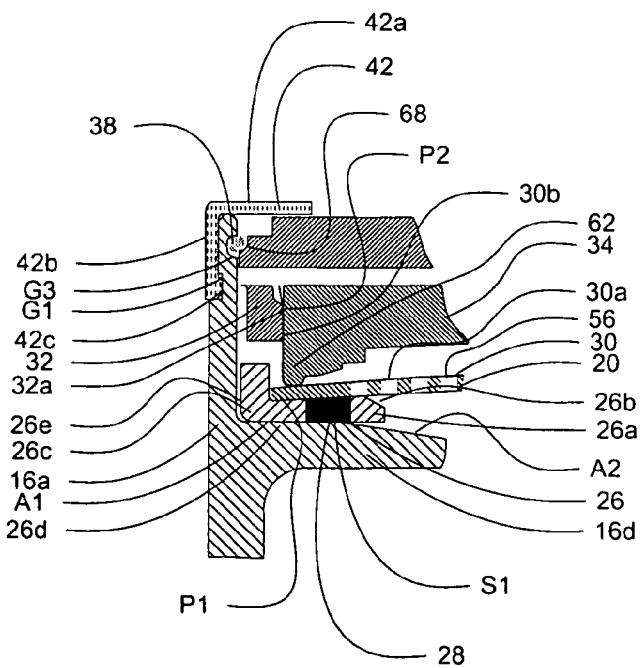
FIG. 3D is an enlarged, fragmentary cross-sectional view similar to that of FIG. 3C showing the "O" ring positioned in a seal seat and compressed.
Figure 9:
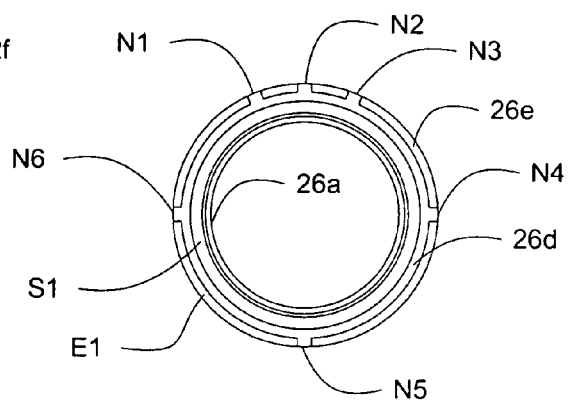
FIG. 9 is a plan view of the seal seat used in the sensor shown in FIG. 1.
Figure 10:
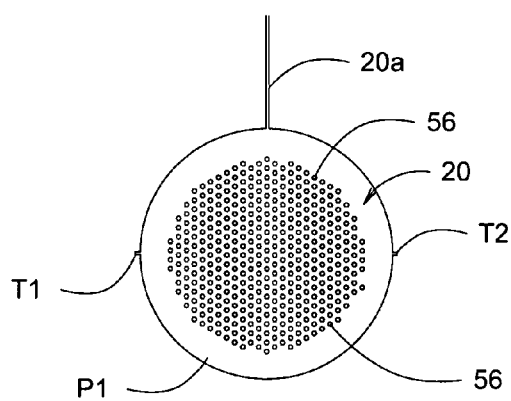
FIG. 10 is a plan view of the cathode used in the sensor shown in FIG. 1.

As best illustrated in FIGS. 3C and 3D, resting on the flat annular platform area A1 of the shelf member 16d is the seal seat 26. The seal seat 26 comprises an inner annular element 26a having a beveled inside edge 26b and a spaced apart outer annular element 26c having sides 26d and 26e at a right angle to each other. As best shown in FIG. 9, there are notches N1, N2, N3, N4, N5, and N6 in the top edge E1 of side 26e. As best shown in FIG. 10, there are tabs T1 and T2 projecting outward from the perimeter P1 of the cathode 20. The notches N4 and N6 are interactive with tabs T1 and T2 upon assembly of the gas entry section 12, so that the tabs T1 and T2 respectively fit within the notches N6 and N4 to prevent rotation of the cathode 20 within the seal seat 26. Upon assembly of the gas entry section 12, the notches N1 and N3 are respectively aligned within the orifices 47 and 45, and the tail element 20a of the cathode 20 sits in the notch N2 and passes through the orifice 44 in the cylindrical housing 16.

As illustrated in FIGS. 3C and 3D, the O" ring 28 is placed in the space Si between the inner annular element 26a and the outer annular element 26c. The O" ring 28, inner annular element 26a, and the outer annular element 26c are all made of an electrically insulating material. As depicted in FIG. 3C, prior to being compressed, the "O" ring 28 has a diameter smaller than the width of the space SI between the inner annular element 26a and the outer annular element 26c, but greater than the thickness of these elements 26a and 26c. As depicted in FIG. 3D, when the gas entry section 12 is assembled, the "O" ring 28 is compressed to deform and completely fill the space SI.

The perforated cathode 20 is positioned to overlie the assembly of the seal seat 26 and O" ring 28 with its perimeter P1 abutting the intersection of the sides 26d and 26e of the outer annular element 26c and its connector tail element 20a projecting through the orifice 44 in the sidewall 16a of the cylindrical housing 16. The inner annular member 26a has a thickness t, greater than the thickness $t_2$ of the side 26d of the outer annular element 26c. Upon assembly when the membrane 30 and cathode 20 are compressed between the seal seat 26 and the retainer plate 34, this differential in thickness assist in maintaining the dome shape of the cathode.

Figure 11:
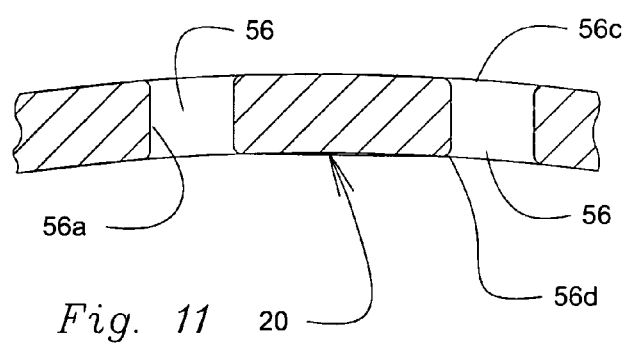
FIG. 11 is an enlarged, fragmentary cross-sectional view of the cathode shown in FIG. 10.

As best shown in FIG. 11, the cathode 20 has a plurality of holes 56 therein having internal sides 56a. The cathode 20 is electrically isolated from the conductive housing 16 but is in contact with the electrolyte 24. The cathode 20, including its connector tail element 20a, is made from a sheet of metal having a thickness from about 0.005 to about 0.020 inch. A commonly employed metal used to make the cathode 20 is copper, nickel, or brass plated with silver. It is desirable that the entrance 56c and exit 56d of the holes 56 be rounded. This avoids the membrane 30 from being pressed into and sealing the holes 56 to prevent electrolyte from flowing into the interface between the cathode 20 and the membrane where the oxidation-reduction reaction occurs. The inside edge 26b of the inner annular element 26a of the seal seat 26 is beveled to avoid or minimize collecting gas at the boundary between the seal seat 26 and the underside of the cathode 20.

As illustrated in FIGS. 3C and 3D, the gas permeable membrane 30 has a cup-like shape with a circular shaped bottom 30a and an upwardly extending annular side 30b. The membrane 30 prevents electrolyte 24 from escaping the chamber 18 but allows gas to permeate it. The thickness of the membrane 30 typically is from about 0.0005 to about 0.005 inches and may be made of a plastic such as, for example, a polyfluorocarbon sold under the trademark Teflon. This material is an electrical insulator, so the cathode 20 is electrically isolated from the housing 16. The bottom 30a of the membrane 30 overlies and substantially covers the entire perforated segment of the cathode 20. Positioned within the inside of the upwardly extending side 30b is the retainer plate 34, which is disk-shaped having a diameter substantially the same as the diameter of the bottom 30a of the membrane 30. This retainer plate 34 may be made of stainless steel.

Figure 2C:
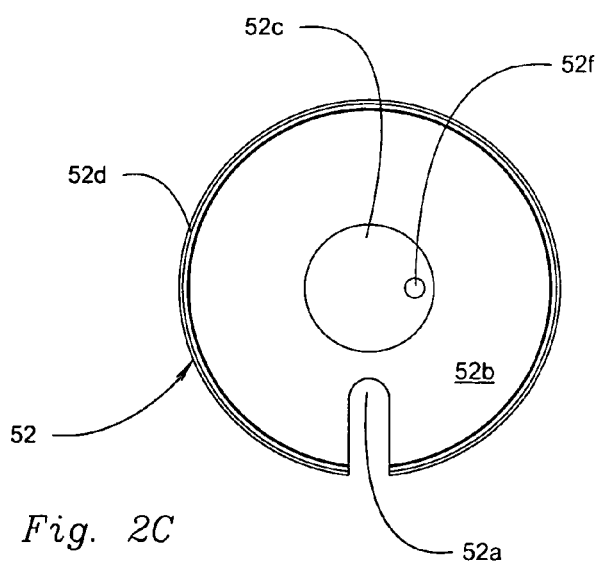
FIG. 2C is a plan view of the underside of a contact plate used in the sensor shown in FIG. 1.
Figure 2A:
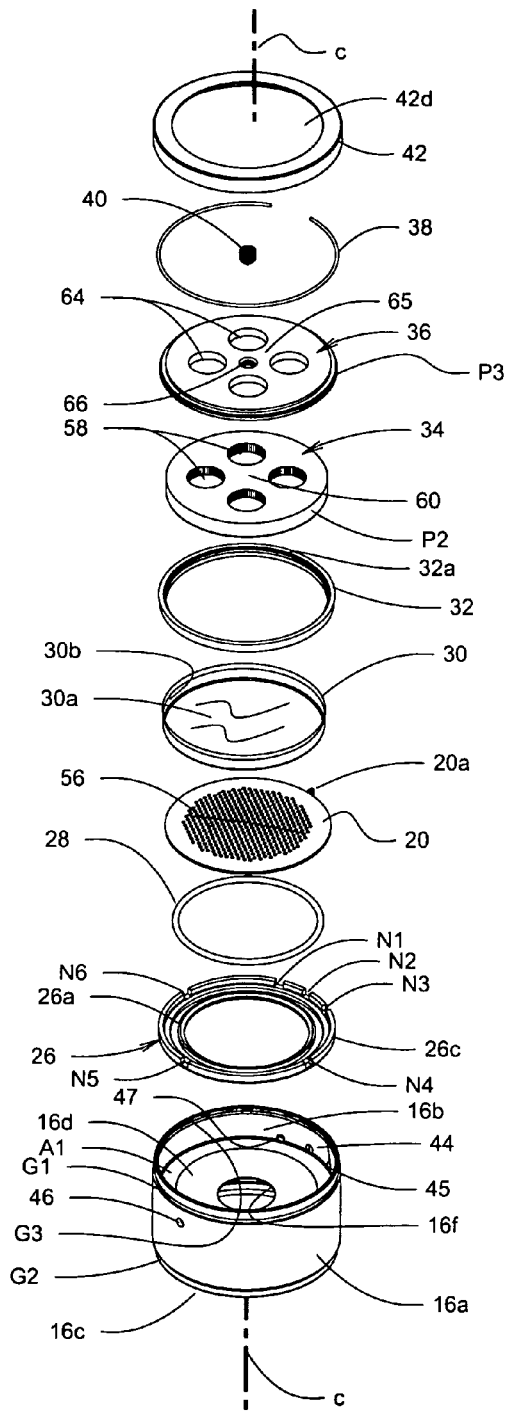
FIG. 2A is an exploded perspective view of the gas entry section of the gas sensor shown in FIG. 1.

As best shown in FIGS. 2A and 3C, within the retainer plate 34 are four gas passages 58 surrounding a central portion 60. The interior of the upwardly extending side 30b of the membrane 30 abuts the perimeter P2 of the retainer plate 34 and the exterior of the upwardly extending side 30b abuts an inside surface 32a of the holding ring element 32. This holding ring element 32 may be made of stainless steel. Optionally, an adhesive may be applied to the interior and exterior of the side 30b to bond this side to the retainer plate 34 and the holding ring element 32. The outer underside edge of the retainer plate 34 has an annular bead 62 with a rounded portion 62a projecting downward in contact with exposed surface of the bottom 30a of the membrane 30. Consequently, the membrane 30 will not be damaged or cut when it is compressed between this bead 62 on the retainer plate 34 and the top surface of the cathode 20.

The cover plate 36 is a disk-like member that has four gas passages 64 surrounding a central portion 65 with a threaded passageway 66 therein. This cover plate 36 may be made of stainless steel. The diameter of the cover plate 36 is about equal to the inside diameter of the cylindrical housing 16 and slightly larger than the diameter of the retainer plate 34. There is a recess 68 in the perimeter P3 of the cover plate 36 that receives an inside portion the C-clip 38 upon assembly. Upon assembly, an outside portion of the C-clip 38 is lodged in the groove G3 on the inside surface of the sidewall 16a of the housing 16.

As best shown in FIGS. 3C and 3D, the insulator end cap 42 has a ring shape with an open center 42d, is made of an insulting material such as, for example, a plastic, and includes an annular top 42a and an annular leg 42b at a right angle to each other. The leg 42b has at its outer terminal end an annular finger 42c. Upon assembly of the gas entry section 12, the end cap 42 snaps over the end 16b of the housing 16 and the annular finger 42c is received in the groove GI next to the open end 16b of the housing 16. The annular top 42a overlaps the top outer edge portion of the cover plate 36 and the open center provides access for gas entering the sensor 10. The setscrew 40 is screwed into the threaded passageway 66 in the cover plate 36.

To assemble the components of the gas entry section 12, the seal seat 26 is placed on the annular platform area A1 of the shelf member 16d with the "O" ring 28 in the space S1 between the inner annular element 26a and outer annular element 26c. The cathode 20 is then placed on the assembly of the seal seat 26 and "O" ring 28, and the inner portion of the tail element 26a is placed in the notch N2 and its terminal end 20b is fed through the orifice 44 so that it extends outward from the housing 16. After the application of adhesive to the interior and exterior of the upwardly extending side 30b of the membrane 30, the holding ring 32, retainer plate 34, and membrane 30 are assembled by sliding the holding ring element 32 over the side 30b to sandwich this side between the retainer plate 34 and the holding ring element, holding the side 30b firmly there between.

The assembly of holding ring 32, retainer plate 34, and membrane 30 is placed on top of the cathode 20. Next, the cover plate 36 is positioned on top of the assembly of the holding ring 32, retainer plate 34, and membrane 30 and rotated until the four gas passages 64 in the cover plate are brought into registration with the four gas passages 58 in the retainer plate 34. The C-clip 38 is now snapped into the groove G3 and the insulator end cap 42 is snapped into position as discussed above. At this point in the assembly, the "O" ring 28 is in an uncompressed state as shown in FIG. 3C. The setscrew 40 is then screwed into the threaded passageway 66 in the central portion of the cover plate 36. As the setscrew 40 advances, its pointed end 40a bears against the central portion 60 of the retainer plate 34, pushing this plate inward towards the cathode 20 so that the rounded portion 62a of the bead 62 presses against the perimeter of the bottom 30a of the membrane 30 to prevent its movement. This also increases slightly the bowing of the domed portion of the cathode 20 to stretch the membrane 30 tightly against the exterior surface of the cathode. Concurrently, the cathode 20 is pushed against the seal seat 26 to compress the "O" ring 28 so that it completely fills the space S1 between the inner annular element 26a and outer annular element 26c.

As shown in FIG. 3D, a gel type sealant such as, for example, an epoxy material, may now used to fill any empty space S2 (a) between the membrane 30 and the side 26e of the outer annular element 26c, (b) between the holding ring 32 and the top of the side 26e, (c) between the holding ring 32 and the inside surface of sidewall 16a, and (d) between the side 26e and the inside surface of sidewall 16a. Any open space surrounding the portion of the tail element 26a of the cathode 26 in the orifice 44 is filled with sealant to close and seal this orifice.

The Closure Section's Components

In addition to the circuit board 54 and contact plate 52, the closure section 14 may include the following components: (a) an insulator end cap 70, (b) a cover member 72 having a gas impermeable, flexible wall portion 72a, and (c) an "O" ring 74.

As best illustrated in FIG. 3B, the insulator end cap 70 is constructed like the end cap 42. It has a ring shape with an open center 70d, is made of an insulting material such as, for example, a plastic, and includes an annular bottom 70a and an annular leg 70b at a right angle to each other. The leg 70b has at its outer terminal end an annular finger 70c.

As best depicted in FIG. 8, the cover member 72 includes a flexible wall portion 72a and a ring member 72b having an external annular groove G4 and a rim 72c. This ring member 72b is made of polyethylene. The flexible wall portion 72a may comprise, for example, a polyethylene sheet material. The perimeter of the wall portion 72a is, for example, bonded to the flat outer edge E2 of the ring member 72b by heat sealing. Upon assembly of the closure section 14, the "O" ring 74 is seated in the groove G4 and bears against the interior surface of the sidewall 16a to form a seal and the rim 72c abuts the annular ledge 16i in the sidewall 16a. The wall portion 72a, upon assembly of the closure section 14, forms one wall of the chamber 18, with the membrane 30 and sidewall 16a forming the other walls of this chamber. The wall portion 72a expands and contracts to compensate for volumetric changes of the electrolyte due to temperature changes.

Figure 2B:
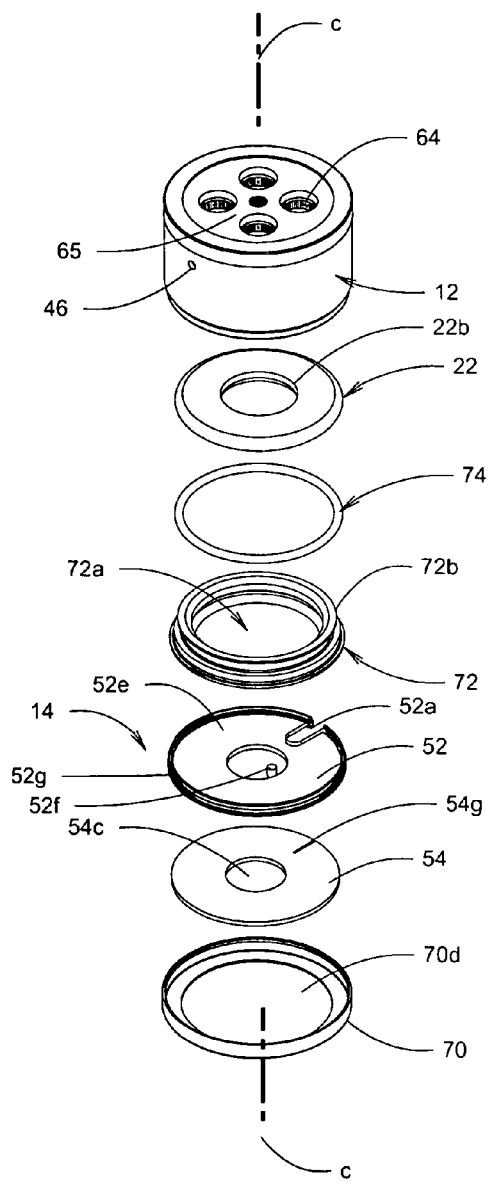
FIG. 2B is an exploded perspective view of the closure section of the gas sensor shown in FIG. 1 prior to being connected to the assembled gas entry section shown in FIG. 2A.

As best shown in FIGS. 2B and 3B, the circuit board 54 is a disk-like member comprising a flat panel member 54b made of an insulating material, with the external, annular electrical conductive lead 54a on its outer surface near its periphery. Due to the annular configuration of the lead 54a (one terminal of the sensor 10), upon insertion of the sensor 10 into the gas-analyzing instrument (not shown), electrical connection with the instrument's one contact (not shown) for this lead 54a may be achieved without any special orientation of the sensor 10 with respect to this one contact. There is a central, circular opening 54c in the circuit board 54 encircled by a raised annular protrusion 54d. Another concentric, raised annular protrusion 54e is at the circuit board's 54 perimeter. A sunken floor 54f lies between these protrusions 54d and 54e providing a space S3 into which the wall portion 72a may expand. A radial slit 54g extends inward from the perimeter of the circuit board 54. The terminal end 20b of the tail element 20a of the cathode 20 extends through the radial slit 54g upon assembly of the closure section 14.

As best shown in FIGS. 2A and 2C, the contact plate 52 is a disk-like member made of metallic material that is gold plated to enhance its conductivity. It has a diameter slightly greater than the diameter of the circuit board 54. The underside 52b (FIG. 2C) of the contact plate 52 includes the outwardly projecting, circular flange 52c and an outer concentric annular flange 52d along the plate's 52 perimeter. A radial slot 52a extends inward from the perimeter of the contact plate 52 and there is an annular step 52g (FIGS. 2B and 6) along this perimeter. A hole 52f extends through the circular shaped flange 52c from the topside 52e to the underside 52b of the contact plate 52. This allows air to escape and enter the space S3 as the wall portion 72a expands and contracts. Upon assembly, the circuit board 54 fits snugly between the flanges 52c and 52d, with the circular shaped flange 52c fitting snug within the circular opening 54c in the circuit board 54 and extending through this opening. The outer flange 52d abuts the perimeter of the circuit board 54. The outer surface of the circuit board, including the lead 54a, is substantially flush with the tops of the flanges 52c and 52d. Upon insertion of the sensor 10 into the gas-analyzing instrument (not shown), electrical connection with the instrument's other contact (not shown) is achieved when the exterior surface of the circular shaped flange 52c (the other terminal of the sensor 10) engages this other contact.

The assembly of the closure section 14 is shown in FIGS. 4 through 6. As depicted in FIG. 4, first the assembled gas entry section 12 is inverted and the anode 22 is formed in situ. Formation of the anode 22 is as follows: With the assembled gas entry section 12 inverted as shown in FIG. 4, a plug 80 is inserted into the central opening 16g in the shelf member 16d, blocking this central opening. Particles of anode material, for example lead, are introduced through the open end 16c of the housing 16. These particles of anode material are deposited on the annular underside surface 16h of the shelf member 16d around the plug 80 in an annular mass. The particles of anode material usually have an average size of from about 0.02 to about 0.04 inch. After a sufficient volume of particles has been deposited around the plug 80, the mass is compacted by pressing the mass firmly against the underside surface 16h to provide, for example, an annular mass having a volume of from about 0.05 to about 0.1 cubic inches. This both forms the anode 22 and bonds it to this surface 16h. Concentric annular ridges 22a are formed in the mass of particles as they are compacted due to the shape of a tool (not shown) that is used to compress the mass during formation the anode 22, which is solid yet porous.

Figure 7:
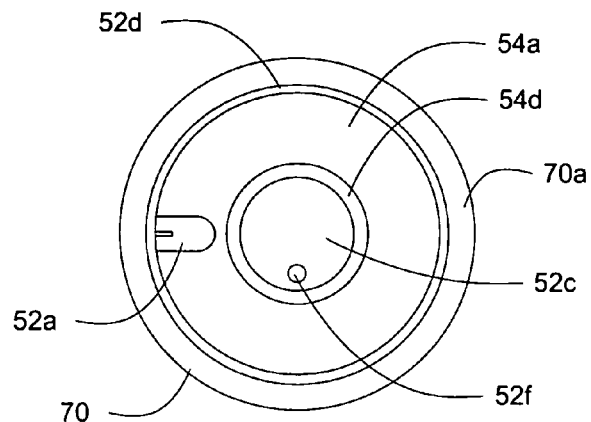
FIG. 7 is a bottom end view of the gas sensor shown in FIG. 1 taken along line 7-7 of FIG. 3A.

As depicted in FIG. 5, the plug 80 is next removed, withdrawing it from a central aperture 22b (FIG. 2B) that has been formed in the anode 22. The electrolyte 24 is introduced into the chamber 18 and the cover member 72 is attached. The cover member 72, including the "O" ring 74 in the annular groove G4, is pushed into the open end 16c until the rim 72c of the ring member 72b abuts the inner annular ledge 16i of the housing 16 and the annular step 52g in the contact plate 52 abuts the outer annular ledge 16j of the housing 16. As depicted in FIG. 6, the assembled contact plate 52 and circuit board 54 is placed in the open end 16c. The assembled contact plate 52 and circuit board 54 are positioned within the open end 16c, with the contact plate being inward of the circuit board. The assembled contact plate 52 and circuit board 54 are advanced until the step 52g in the contact plate 52 abuts the outer annular ledge 16j of the housing 16. The "O" ring 74 is now compressed to hold the cover member 72 in the position as shown in FIG. 5. And finally, the end cap 70 is attached by snapping it over the end 16c of the housing 16 with the annular finger 70c received in the groove G2 next to the now closed end 16c of the housing 16. As shown in FIG. 7, the annular bottom 70a of the end cap 70 overlaps an outer edge portion of the circuit board 54.

Alternate Embodiment

Figure 12A:
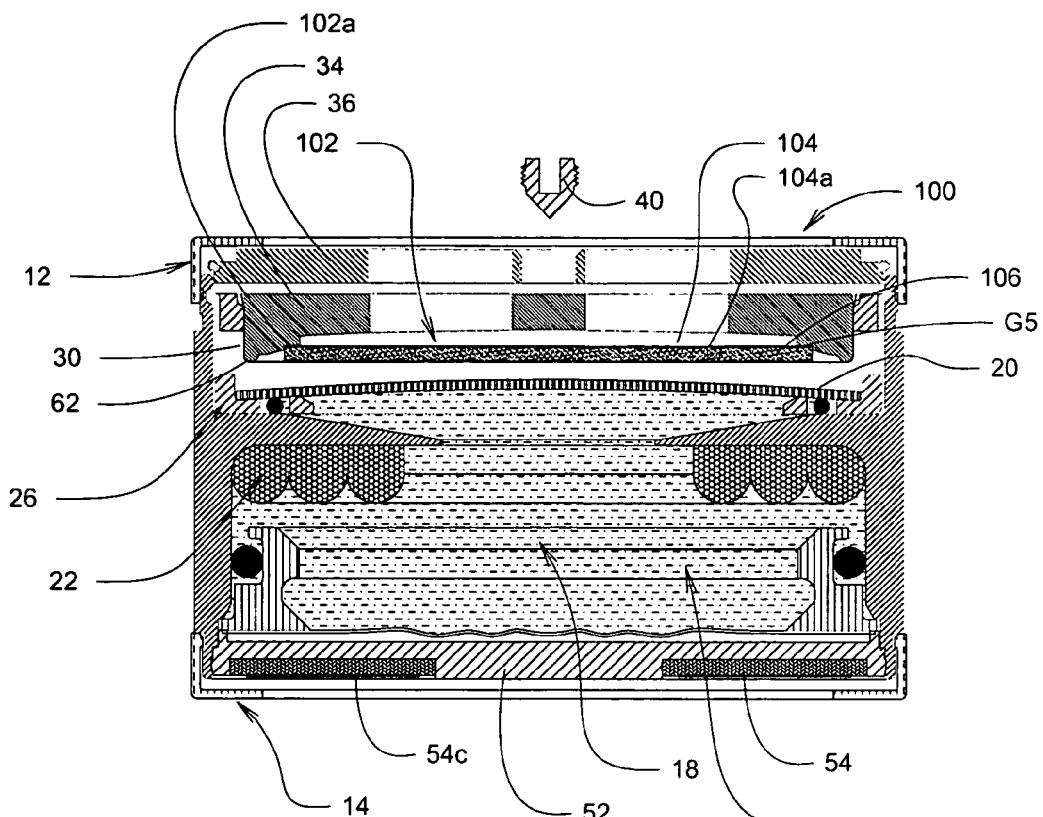
FIG. 12A is a cross-sectional view of an alternate embodiment of the sensor of this invention that is partially assembled, showing a pressure control structure positioned to contact a side of the membrane not in intimate contact with the cathode.

In FIG. 12A another embodiment of this invention, the sensor 100, is depicted that may be used to minimize or avoid separation of the membrane 30 from the cathode 20 when internal pressure in the chamber 18 is at an excessively high level. In some cases, when switching between analyzing gas streams of differing composition, an excessively high pressure may develop within the chamber 18. For example, upon switching between a gas stream containing a mixture of oxygen and nitrogen and a gas stream containing a mixture of oxygen and helium. Nitrogen diffuses very slowly across the membrane 30 relative to the rate of diffusion of helium. Thus, the electrolyte 24 will initially contain both nitrogen and helium as the gas stream containing a mixture of oxygen and helium is being analyzed. This results in an increase in pressure that endures for a period of time until most of the nitrogen is eventually replaced by helium. This increase in internal pressure in the chamber 18 could cause the membrane 30 to be pushed away from the cathode 20, ending their intimate contact.

Figure 12B:
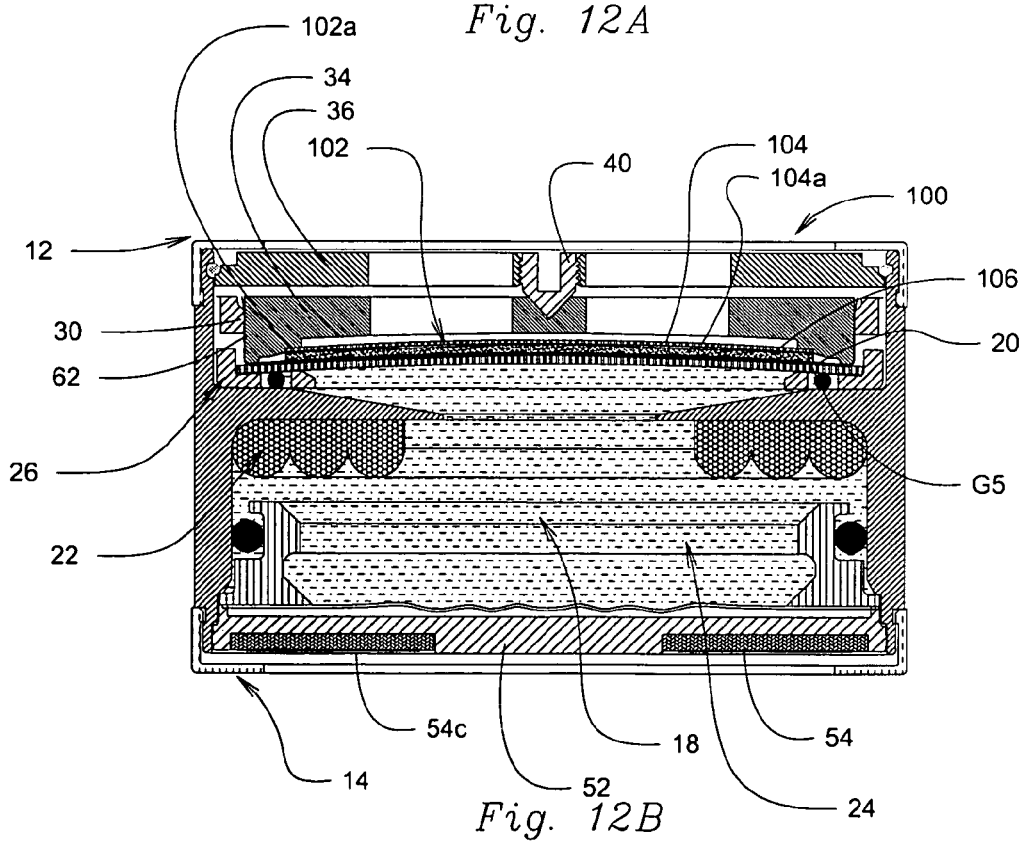
FIG. 12B is a cross-sectional view similar to that shown in FIG. 12A of the completely assembled sensor, showing the pressure control structure in contact with the side of the membrane not in intimate contact with the cathode.

In the sensor 100, a pressure control structure 102 is located between the membrane 30 and the retainer plate 34. The pressure control structure 102 may be multi-layered, comprising an outer, flexible metal disk-shaped spring member 104 overlying an inner porous, disk-shaped cushion member 106. The spring member 104 has openings 104a therein that allows gas to pass through it and then through the cushion member 106. This cushion member 106 may be made of a polyfluorocarbon sold under the trademark Zytex. The perimeter 102a of the pressure control structure 102 abuts an internal annular groove G5 in the retainer plate 34. Upon assembly of the gas entry section 12 as discussed above, the pressure control structure 102 flexes and conforms to the dome shape of the cathode 20 as shown in FIG. 12B. The flexible spring member 104 is deformed into a concave shape and is now in tension, pushing across the surface of the membrane 30 with a substantially uniform inward force to press the membrane against the cathode 20 to counteract any excessive internal pressure in the chamber 18 that could cause the membrane 30 to be pushed away from the cathode.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

The invention claimed is:

1. A gas sensor comprising
a housing including a shelf member and a chamber containing an electrolyte, said housing and shelf member being made of a metallic material,
a cathode mounted on the shelf member, said cathode having a plurality of holes therein and including a conductive tail element,
a gas permeable membrane overlying the cathode that prevents electrolyte escaping the chamber but allows gas to permeate the membrane, and an anode within the chamber that is spaced from the cathode and is in electrical contact with the electrolyte and the conductive housing, said tail element of the cathode being adapted to be connected to the anode through an electrical circuit including the metallic housing upon use of the sensor with a gas-analyzing instrument, the shelf member has a topside, an underside, and a central opening, and the anode is in electrical contact with the underside and has a central aperture in communication with the central opening in the shelf member.

2. The gas sensor of claim 1 where the topside includes a portion that slants inward towards the central opening.

3. The gas sensor of claim 1 where the housing includes a sidewall that partially forms the chamber, said housing having first and second opposed ends.

4. The gas sensor of claim 3 where the shelf member is integral with the sidewall, is disposed between said first and second opposed ends, and projects inward from the sidewall.

5. The gas sensor of claim 3 where the ends are capped with insulator members.

6. The gas sensor of claim 3 where the tail element extends through an orifice in the sidewall and has a terminal end adapted to be electrically connected in said circuit.

7. The gas sensor of claim 3 where the second end includes a flexible portion that expands and contracts as the temperature of the electrolyte changes to compensate for volumetric changes of the electrolyte.

8. The gas sensor of claim 1 where the cathode, including said tail element, is made from a sheet of metal having a thickness from 0.005 to 0.020 inch.

9. The gas sensor of claim 1 where the cathode is isolated from the conductive housing and shelf member by an electrical insulating structure including the membrane.

10. The gas sensor of claim 9 where the cathode and membrane are disposed between first and second compression elements, with the cathode and membrane each having an outer portion sandwiched between said compression elements.

11. The gas sensor of claim 10 where the first compression element includes an outer annular spacer member made of an insulating material and positioned on the shelf member, said outer annular spacer member having first and second walls substantially at a right angle to each other, said first wall abutting the sidewall of the housing and the second wall abutting the shelf member, an inner annular member made of an insulating material and positioned on the shelf member and positioned within the outer annular spacer member and concentric therewith, said inner annular member being spaced from the second wall to provide an annular gap between the inner annular member and said second wall, and an "O" ring seated in the annular gap.

12. The gas sensor of claim 11 where second wall has a predetermined thickness and the inner annular member has a thickness greater than said predetermined thickness of the second wall.

13. The gas sensor of claim 11 where the "O" ring seated in the annular gap is compressed to substantially fill said gap and provide a seal.

14. The gas sensor of claim 10 where the second compression element includes an outer member with a rounded portion engaging the membrane during compression of said membrane.

15. The gas sensor of claim 1 where housing includes a sidewall having a maximum thickness of 3/16 inch.

16. The gas sensor of claim 1 including a retainer structure that stretches the membrane.

17. The gas sensor of claim 16 where the retainer structure comprises an inner member covering a central portion of the membrane and an outer member into which the inner member fits snugly, said membrane having a marginal edge portion that fits between the inner and outer members and is held firmly there between, said inner member being open to allow gas to permeate through said central portion of the membrane.

18. The gas sensor of claim 11 where the membrane has one side that is in intimate contact with the cathode and said sensor includes a pressure control structure adjacent to and overlying the other side of the membrane that is not in intimate contact with the cathode, said pressure control structure forcing the membrane into intimate contact with the cathode and being opened to allow gas to pass therethrough.

19. The gas sensor of claim 18 where the pressure control structure comprising an outer, flexible metal disk-shaped spring member with openings therein that overlies a porous, disk-shaped cushion member.

20. A gas sensor including an electrically conductive metallic housing including a chamber containing an electrolyte, said housing having a cylindrical sidewall and an annular shelf member projecting inward from the sidewall substantially at a right angle thereto and having an inner edge defining a central opening in said shelf member, a metallic, substantially disk shaped, substantially domed cathode having a plurality of holes therein, said cathode being on one side of the shelf member and overlying the central opening in said shelf member and isolated from the housing by an electrical insulating structure, said cathode including a conductive metallic tail element that extends through an orifice in the sidewall and has a terminal end, said tail element being electrically insulated from the side wall, a thin walled, gas permeable, non-conductive membrane overlying the cathode and in intimate contact therewith that prevents electrolyte escaping the chamber but allows gas to permeate the membrane, and an anode on another side of the shelf member in contact with the electrolyte, said anode having a central aperture concentric with the central opening in said shelf member, said tail element of the cathode being adapted to be connected to the anode through an electrical circuit including the conductive housing upon use of the sensor with a gas-analyzing instrument, a retainer structure that stretches the membrane, said retainer structure comprising an inner member that the membrane covers and an outer member into which the inner member fits snugly, said membrane having a marginal edge that fits between the inner and outer members and is held firmly there between.

21. The gas sensor of claim 20 where the housing has opposed open ends, each said end having an insulator member and each said end being closed and sealed to at least in part form the chamber.

22. The gas sensor of claim 20 where the anode comprises compacted metallic particles.

23. The gas sensor of claim 20 where the cathode, including said tail element, is made from a sheet of metal having a thickness from 0.005 to 0.020 inch.

24. The gas sensor of claim 20 including a pair of compression elements, and the cathode and membrane each having an outer portion sandwiched between the compression elements.

25. The gas sensor of claim 20 including a cover member at an end of the housing having a flexible portion that expands and contracts as the temperature of the electrolyte changes to compensate for volumetric changes of the electrolyte.

26. A gas sensor including
an electrically conductive metallic housing having a sidewall terminating in opposed first and second opens ends,
a conductive shelf member within the housing between the first and second opens ends that projects inward from the sidewall and has a topside, an underside, and an inner edge defining an opening in said shelf member,
a cathode having a plurality of holes therein, said cathode being on the topside of the shelf member and overlying the opening in said shelf member and isolated from the housing and shelf member by an electrical insulating structure,
a thin walled gas permeable membrane overlying the cathode and in intimate contact therewith, and
an anode on the underside of the shelf member having an aperture in communication with the opening in said shelf member,
said cathode and electrical insulating structure first being attached to the first end, next inverting the housing to expose the underside of the shelf member, and then forming on said underside said anode by compacting metallic particles.

27. The gas sensor of claim 26 including cover member that covers the second open end, said cover member having a flexible portion that expands and contracts as the temperature of the electrolyte changes to compensate for volumetric changes of the electrolyte.

28. The gas sensor of claim 27 where the cover member is attached to the second open end after the formation of the anode.

29. The gas sensor of claim 28 where the cathode includes an elongated conductive tail element that extends through in the sidewall.

30. The gas sensor of claim 29 where said first and second ends each has an insulator member.

31. A gas sensor including
an electrically conductive metallic housing including a shelf member and a chamber containing an electrolyte,
a cathode within the chamber that is electrically insulated from the housing and open to allow gas the pass therethrough,
a thin walled, gas permeable membrane overlying the cathode and in intimate contact therewith that prevents electrolyte escaping the chamber but allows gas to permeate the membrane,
an anode in the chamber and spaced from the cathode that is in electrical contact with the electrolyte and the housing,
a first terminal including an electrical conducting member connected to the cathode that enables the sensor to make electrical contact with one contact of a gas-analyzing instrument, and
a second terminal including an electrical conducting member that enables the sensor to make electrical contact with another contact of the gas-analyzing instrument,
said shelf member having a topside, an underside, and a central opening, and the anode being in electrical contact with the underside and having a central aperture in communication with the central opening in the shelf member.

32. A gas sensor comprising
a conductive metallic housing having a shelf member and including means for forming within the housing a sealed chamber containing an electrolyte,
a cathode with holes therein mounted on the shelf member and having means for electrically insulating the cathode from the housing and shelf member,
a gas permeable membrane overlying the cathode that prevents electrolyte escaping the chamber but allows gas to permeate the membrane, and
an anode within the chamber that is spaced from the cathode and is in electrical contact with the electrolyte and the conductive housing, and
means for connecting the cathode to the anode through an electrical circuit including the conductive housing upon use of the sensor with a gas-analyzing instrument and said shelf member having a topside, an underside, and a central opening, and the anode being in electrical contact with the underside and having a central aperture in communication with the central opening in the shelf member.

33. The gas sensor of claim 32 where the housing and shelf member are an integral, unitary structure.

34. The gas sensor of claim 32 where the anode is formed in situ in the chamber.

35. A gas sensor including
a metallic housing formed by a wall member having a maximum thickness of 3/16 inch and including a metallic shelf member,
a chamber containing an electrolyte within the housing,
an open cathode within the chamber that is electrically insulated from the housing,
a thin walled, gas permeable membrane overlying the cathode and in intimate contact therewith that prevents electrolyte escaping the chamber but allows gas to permeate the membrane,
an anode in the chamber and spaced from the cathode that is in electrical contact with the electrolyte and the housing,
a first terminal including an electrical conducting member connected to the cathode that enables the sensor to make electrical contact with one contact of a gas-analyzing instrument, and
a second terminal including an electrical conducting member that enables the sensor to make electrical contact with another contact of the gas-analyzing instrument,
said shelf member having a topside, an underside, and a central opening, and the anode being in electrical contact with the underside and having a central aperture in communication with the central opening in the shelf member.

36. The gas sensor of claim 35 where the first and second terminals are seated on a circuit board connected to the housing.

37. A gas sensor including
a metallic housing including a metallic shelf member,
a chamber containing an electrolyte within the housing,
an open cathode within the chamber that is electrically insulated from the housing, a thin walled, gas permeable membrane overlying the cathode and in intimate contact therewith that prevents electrolyte escaping the chamber but allows gas to permeate the membrane, an anode in the chamber and spaced from the cathode that is in electrical contact with the electrolyte and the housing, and a circuit board connected to the housing comprising a first terminal including an electrical conducting member connected to the cathode that enables the sensor to make electrical contact with one contact of a gas-analyzing instrument, and a second terminal including an electrical conducting member that enables the sensor to make electrical contact with another contact of the gas-analyzing instrument, said shelf member having a topside, an underside, and a central opening, and the anode being in electrical contact with the underside and having a central aperture in communication with the central opening in the shelf member.

* * * * *